United States Patent [19]
Guichardant et al.

[11] Patent Number: 5,158,975
[45] Date of Patent: Oct. 27, 1992

[54] USE OF STEARIDONIC ACID

[75] Inventors: Michel Guichardant, Pully; Michel Rigaud, Limoges, both of France

[73] Assignee: Nestec S.A., Vevey, Switzerland

[21] Appl. No.: 690,492

[22] Filed: Apr. 24, 1991

[30] Foreign Application Priority Data

May 23, 1990 [EP] European Pat. Off. ........ 90109883.0

[51] Int. Cl.$^5$ ............................................. A61K 31/19
[52] U.S. Cl. .................................................... 514/560
[58] Field of Search ......................................... 514/560

[56] References Cited

FOREIGN PATENT DOCUMENTS

0347056A1 12/1989 European Pat. Off. .

OTHER PUBLICATIONS

Chem. Abst. 113-158684(n) (1990).
Ser. No. 07/446130, Dec. 5, 1989, Crozier-Willi et al.
Lee et al. "Effects of Exogenous Arachidonic, Eicosapentaenoic, and Docosahexaenoic Acids on the Generation of 5-Lipoxygenase Pathway Products by Ionophore-Activated Human Neutrophils", *J. Clin. Invest.* 74:1984, pp. 1922-1933.
Tate et al., "Suppression of Acute and Chronic Inflammation by Dietary Gamma Linolenic Acid", *The Journal of Rheumatology*, 16:6, 1989, pp. 729-734.

Primary Examiner—S. J. Friedman
Attorney, Agent, or Firm—Vogt & O'Donnell

[57] ABSTRACT

Stearidonic acid is administered to mammals for inhibiting biosynthesis of leukotrienes.

9 Claims, No Drawings

USE OF STEARIDONIC ACID

BACKGROUND OF THE INVENTION

This invention relates to the use of stearidonic acid an anti-inflammatory pharmaceutical composition.

Stearidonic acid (SA, C18:4 Δ6,9,12,15) is a polyunsaturated fatty acid of the n-3 series (nomenclature defined by the position of the first double bond from the methyl group). To be utilized by the organism, α-linolenic acid (ALA, C18:3 Δ9,12,15), which is the starting point of the n-3 series and which is present in the majority of ingested diets, has to be metabolized into SA by desaturation by means of the enzyme Δ6 desaturase. Now, it is known that the activity of this enzyme is weak and that it diminishes with age and after certain disorders.

Among the substances playing an important part in inflammatory processes, for example of the allergic type, such as asthma, of the cutaneous type, such as acne, psoriasis and eczema, or of the rheumatic type, as well as those following traumatisms, states of shock or pathologies, such as mucoviscidose for example, leukotrienes are formed mainly by oxidation by the lipoxygenases of arachidonic acid (AA, C20:4 Δ5,8,11,14) which is released from cell membranes. More particularly, it is known that poly-morphonucleated human leukocytes transform AA into leukotrienes more particularly into stable (5S,12R)-5,12-dihydroxy-6,14-cis-8,10-trans-eicosatetraenoicacid (LTB4), by way of 5-lipoxygenase. LTB4 plays a predominant part in various inflammatory processes.

For this reason, attempts have been made to reduce the inflammation factors by developing inhibitors of 5-lipoxygenase. It has been shown, for example by Lee, T. H. et al, (1984) in J. Clin. Invest 74, 1922–1933, that certain higher fatty acids of the n-3 series, such as eicosapentaenoic (EPA, C20:5 Δ5,8,11,14,17), are able to modulate the synthesis of the leukotrienes and to improve the inflammatory conditions. This was also demonstrated for a fatty acid of the n-6 series, dihomo-γ-linolenic acid (DHLA, C20:3 Δ8,11,14), see for example Tate, G. et al, (1989) in J. Rheumatol. 16, 729–733.

SUMMARY OF THE INVENTION

Applicants have found that SA has the property of inhibiting the biosynthesis of leukotrienes.

The present invention is particularly characterized in that stearidonic acid is administered to mammals orally, rectally, enterally, or parenterally in an amount effective for inhibiting biosynthesis of leukotrienes.

DETAILED DESCRIPTION OF THE INVENTION

Accordingly, the present invention relates to the use of stearidonic acid or any of its pharmaceutically acceptable derivatives for the preparation of a pharmaceutical composition intended for the prevention and treatment of disorders of inflammatory origin in mammals, more particularly allergic disorders, skin disorders, rheumatic disorders and those following traumatisms, states of shock and pathologies.

In the context of the invention, a pharmaceutically acceptable derivative is understood to be a salt, ester or amide corresponding to the fatty acid. Preferred salts are the salts of amino acids, for example arginine. Preferred esters are, for example, the mono-, di- or triglycerides and the phospholipides.

In one particular embodiment, the SA is used in combination with one or more polyunsaturated fatty acids which inhibit the oxygenated metabolism of AA. This unsaturated fatty acid may be a 5-lipoxygenase-inhibiting polyunsaturated fatty acid of the n-3 series, for example EPA, docosahexaenoic acid (DHA, C22:6 Δ4,7,10,13,16,19), or of the n-6 series, for example DHLA or its precursor γ-linolenic acid (GLA, C18:3 Δ6,9,12), or even a pharmaceutically acceptable derivative of such a fatty acid of the type defined above.

One preferred embodiment of this combined use is characterized by the use of a concentrate essentially containing GLA and SA from blackcurrant seed oil, for example prepared in accordance with Example 1.2 of EP-A-0399417.

Another preferred embodiment of this combined use is characterized by the use of a concentrate essentially containing SA, EPA and DHA from fish oil, for example prepared in accordance with the first paragraph of Example 3 of EP-A-0399417.

The SA or the mixture of polyunsaturated fatty acids or their derivatives used in accordance with the invention may advantageously be protected against oxidation by an anti-oxidant, for example ascorbyl palmitate, tocopherols, ascorbic acid in the presence of lecithin or a mixture of such antioxidants.

The pharmaceutical composition may be formulated in various ways according to the method of administration, for example oral, enteral, rectal, or parenteral for administration to mammals. For example, the pharmaceutical composition may be formulated as capsules, gelatine-coated tablets, suppositories or syrups. For enteral or parenteral administration, the composition is formulated as chemically and physically stabilized, apyrogenic and sterile solutions or emulsions.

A pharmaceutical composition may be formulated for topical administration. In the particular case of topical application, for example for treating dermatological inflammations of the acne, eczema or psoriasis type, the composition may be formulated, for example, as an ointment, a salve, cream or lotion.

The dose administered will depend upon the type and degree of the disorder to be treated. It may amount to between 0.05 and 10 g stearidonic acid per day in a single dose or preferably in 2 to 3 separate doses.

EXAMPLES

The invention is illustrated by the following Examples in which parts and percentages are by weight, unless otherwise indicated.

EXAMPLE 1

Effect of SA on the biosynthesis of leukotrienes

To study the effect of SA on the biosynthesis of leukotrienes, isolated human leukocytes are incubated with SA and, by way of comparison with EPA and DHLA, the metabolites produced by the action of 5-lipoxygenase on AA are identified by two-dimensional thin-layer chromatography (TLC) and are quantitatively analyzed by high-performance liquid chromatography (HPLC).

To follow the metabolisms of AA and SA, certain experiments were carried out with these fatty acids labelled with C14 in the C1 position.

Experimental conditions

Preparation of the cell suspensions

Blood from normal donors who have taken no medicaments for at least 10 days before donating their blood is collected on a mixture of citric acid, trisodium citrate and dextrose as anticoagulant. After centrifugation at 200 G for 15 mins., the plasma rich in platelets is eliminated and the remaining blood fraction is collected and 0.5 volume of an aqueous solution containing 3% dextran 250 and 0.9% NaCl is added thereto. The red globules are left to sediment for about 90 minutes at ambient temperature after which the supernatant is collected and centrifuged at 80 g for 15 minutes. The sediment obtained, which corresponds to approximately $2 \times 10^6$ cells, is then re-suspended for 15 s in 1 ml distilled water, after which iso-osmolarity is re-established by addition of 1 ml of $2\times$ concentrated Tyrode/HEPES solution. The suspension is then centrifuged at 60 g for 10 minutes, a sediment of leukocytes is collected and is then re-suspended in a Tyrode/HEPES solution containing 2 mM (mmol/l) calcium.

After the leukocytes have been stimulated with ionophoric calcium A23187 (1 $\mu$M), with AA(20 $\mu$M) for 10 minutes at 37° C., they are incubated with the fatty acids (optionally labelled with C14 in the 1 position for SA or AA) in the quantities indicated below in paragraph 2 for 30 minutes at 37° C. Incubation is terminated with ethanol containing 2 nanomoles 13-hydroxyoctadecadienoic acid (13-HODE) (obtained by the action of soya lipoxygenase on linoleic acid) and 2 nanomoles prostaglandin B2 (PGB2) in a quantity of 3 times the volume of ethanol relative to the volume of the suspension The lipids are extracted with chloroform in a quantity of 6 times the volume of the suspension (without ethanol). 13-HODE and PGB2 are used as standards for quantitative analysis.

Analysis of the monohydroxylated fatty acids

The extracted lipids are separated by two-dimensional thin-layer chromatography on plates of silica gel G. The monohydroxylated fatty acids are developed in the first dimension with a solvent mixture of hexane, diethyl ether and glacial acetic acid in a ratio by volume of 59:40:1, the dihyroxylated fatty acids remaining at the beginning of the plate. Those monohydroxylated fatty acids which have been labelled with a radioactivity detector are detected, collected from the plate along with the 13-HODE, extracted with diethyl ether and, after evaporation of the solvent under nitrogen, are separated by reverse-phase HPLC with an elution solvent mixture of methanol and aqueous acetic acid, pH3, in a ratio by volume of 73:27. They are detected by UV spectroscopy at a wavelength 234 nm and are quantified by comparison with the 13-HODE standard on the basis of the hypothesis that they all have the same specific extinction of $3 \times 10^4$ $M^{-1}cm^{-1}$.

Analysis of the dihydroxlated fatty acids

The dihydroxylated fatty acids remaining at the beginning of the plate are developed in the second dimension perpendicularly to the first using a solvent mixture of hexane, diethyl ether and glacial acetic acid in a ratio by volume of 25:74:1. Their detection, collection, extraction, separation and quantitative analysis are carried out in the same way as described in 1 2 above, except that the elution solvent mixture used in the HPLC is a mixture of methanol and aqueous acetic acid, pH3, in a ratio by volume of 66:34. PGB2 is used as standard in the quantitative evaluation of the dihydroxylated fatty acids according to their respective maximum UV absorptions (wavelengths 270 nm, extinction $2.8 \times 10^4$ and $5 \times 10$ $M^{-1} cm^{-1}$ for $PGB_2$ and dihydroxy derivatives, respectively).

Results

Arachidonic acid (AA) (Sigma Chemical Company, St. Louis, Mo./USA) is used as control, i.e. the leukocytes are not incubated with other fatty acids.

The fatty acids incubated with the leukocytes are: stearidonic acid (SA) obtained from the oil of blackcurrant seed oil in purified form in accordance with EP-A-0399417, eicosapentaenoic acid (EPA) (Sigma Chemical Company) and dihomo-$\gamma$-linolenic acid (DHLA) (Sigma Chemical Company).

5-Hydroxyeicosatetraenoic acid (5-HETE) (Cayman Chemical, Ann Arbor, Mich./USA), maximum wavelength ($\lambda$max): 234 nm, retention time (Rt): 42.69 mins., 5S,12S[E,Z,E,Z]-dihydroxyeicosatetraenoic acid (di-HETE) (M. Guichardant et al, Biochem. J., 256, 879–883, 1988), $\lambda$max, 259, 268 and 279 nm, Rt: 29.96 mins., 5S,12R[Z,E,E,Z]-5,12-dihydroxy-6,14-cis-8,10-trans-eicosatetraenoic acid (LTB4) (Cayman Chemical), $\lambda$max: 261, 271 and 282 nm, Rt: 27.46 mins., the A isomer of LTB4, 5S,12R [E,E,E,Z]-LTB4 (M. Guichardant et al. Biochem. J., 256, 879–883, 1988), Rt: 21.46 mins. and the B isomer of LTB4, 5S,12S [E,E,E,Z]-LTB4 (M. Guichardant et al, Biochem. J., 256, 879–883, 1988), Rt: 24.27 mins.

The quantities of metabolites obtained are expressed in picomole/$10^8$ leukocytes and represent the average of 5 experiments with n determinations. The degrees of significance P are determined by a test t in relation to the control.

The results are shown in the following Table:

TABLE

| Fatty acid incubated with the leukocytes stimulated by AA | Quantity of incubated fatty acid, $\mu$m | n | Quantity of metabolites, picomole/$10^8$ leukocytes | | | | |
|---|---|---|---|---|---|---|---|
| | | | 5-HETE | LTB4 | LTB4 A isomer | LTB4 B isomer | DI-HETE |
| SA | 10 | 4 | 8880 | 10220 | 2670 | 2780 | 700 |
| | | | — | $P < 0.02$ | — | — | — |
| SA | 20 | 6 | 7030 | 8480 | 2070 | 2200 | 510 |
| | | | $P < 0.05$ | $P < 0.01$ | $P < 0.01$ | $P < 0.05$ | — |
| EPA | 20 | 4 | 5920 | 9090 | 2180 | 2730 | 510 |
| | | | $P < 0.01$ | $P < 0.01$ | $P < 0.05$ | — | — |
| DHLA | 20 | 3 | 5350 | 3140 | 770 | 780 | 168 |
| | | | $P < 0.01$ | $P < 0.01$ | $P < 0.02$ | $P < 0.05$ | $P < 0.01$ |

TABLE-continued

| Fatty acid in-cubated with the leukocytes stimulated by AA | Quantity of incubated fatty acid, μm | n | Quantity of metabolites, picomole/$10^8$ leukocytes | | | | |
|---|---|---|---|---|---|---|---|
| | | | 5-HETE | LTB4 | LTB4 A isomer | LTB4 B isomer | DI-HETE |
| Control | 0 | 6 | 9080 | 17770 | 4080 | 4190 | 720 |

Legend: —: non-significant

The above results clearly show that SA, a polyunsaturated fatty acid of the n-3 series, has an effect on the metabolism of AA which leads to the leukotrienes by way of the 5-lipoxygenase of human leukocytes. It reduces the formation of 5-HETE and DI-HETE by approximately 25% and the formation of B4 leucotrienes by approximately 50%, i.e., to a level comparable with EPA, which is also a polyunsaturated fatty acid of the n-3 series, for the same concentration (20 μm).

However, its activity is not as strong as that of dihomo-γ-linolenic acid, a polyunsaturated fatty acid of the n-6 series, which inhibits the formation of B4 leucotrienes by approximately 80% and the formation of 5-HETE by approximately 40% for the same concentration (20 μm).

Its effect could also be attributable to some of its hydroxylated metabolites which were detected from labelled SA.

EXAMPLES 2 TO 5

2. Gelatine capsules for oral administration containing 250 mg SA obtained from blackcurrant seed oil are prepared.

3. Gelatine capsules for oral administration containing 250 mg SA obtained from fish oil are prepared.

4. Gelatine capsules for oral administration containing 500 mg of a mixture of fatty acids containing 80% GLA and 15% SA obtained from blackcurrant seed oil are prepared. 5. Gelatine capsules for oral administration containing 500 mg of a mixture of fatty acids containing 16% SA, 35% EPA and 39% DHA from fish oil are prepared.

EXAMPLES 6 TO 9

The following compositions intended for topical application are prepared:

| | % |
|---|---|
| 6. Water-repellent salve | |
| SA | 5 |
| Micronized polyethylene | 10 |
| Isopropyl myristate | 85 |
| 7. Water-repellent ointment | |
| SA | 1 |
| Triglycerides of capric, caprylic and stearic acids | 40 |
| Triglycerides of capric and caprylic acids | 30 |
| Vaseline | 20 |
| Vaseline oil | 9 |
| 8. Cream | |
| SA | 0.5 |
| Cetyl alcohol, cetyl alcohol ethoxylated with 20 mol ethylene oxide, glycerol monostearate | 6 |
| Triglycerides of capric and caprylic acids | 15 |
| Propylene glycol | 10 |
| Water | 68.5 |
| 9. Lotion | |
| SA | 0.1 |
| Ethanol | 50 |
| Propylene glycol | 49.9 |

The compositions of Examples 6 to 9 above are prepared and stored in an inert atmosphere away from light.

We claim:

1. A method for treatment of disorders of inflammatory origin comprising administering stearidonic acid orally to a mammal in need of such treatment in an amount effective for inhibiting biosynthesis of leukotrienes.

2. A method for treatment of disorders of inflammatory origin comprising administering stearidonic acid rectally to a mammal in need of such treatment in an amount effective for inhibiting biosynthesis of leukotrienes.

3. A method for treatment of disorders of inflammatory origin comprising administering stearidonic acid enterally to a mammal in need of such treatment in an amount effective for inhibiting biosynthesis of leukotrienes.

4. A method for treatment of disorders of inflammatory origin comprising administering stearidonic acid parenterally to a mammal in need of such treatment in an amount effective for inhibiting biosynthesis of leukotrienes.

5. A method according to claim 1 or 2 or 3 or 4 wherein the stearidonic acid is in a form selected from a group consisting of pharmaceutically acceptable salts, esters and amides of stearidonic acid.

6. A method according to claim 1 or 2 or 3 or 4 wherein the stearidonic acid is administered in a daily dose of an amount of from 0.5 g to 10 g stearidonic acid.

7. A method according to claim 1 or 2 or 3 or 4 further comprising administering the stearidonic acid with at least one fatty acid which inhibits oxygenated metabolism of arachadonic acid.

8. A method according to claim 7 wherein the at least one fatty acid is selected from the group of fatty acids consisting of eieosapentaenoic acid, and docosahexaenoic acid and combinations thereof.

9. A method according to claim 7 wherein the at least one fatty acid is selected from the group of fatty acids consisting of γ-linolenic acid and idihomo-γ-linolenic acid.

* * * * *

UNITED STATES PATENT AND TRADEMARK OFFICE
CERTIFICATE OF CORRECTION

PATENT NO. : 5,158,975

DATED : October 27, 1992

INVENTOR(S) : Michel Guichardant, et. al.

It is certified that error appears in the above-indentified patent and that said Letters Patent is hereby corrected as shown below:

On the Title page, item [75], inventor: col. 1, line 1, after "Pully", insert --, Switzerland--, and in line 2, delete"both of" ---.

Column, 4, line 6, "dihydroxlated" should be --dihydroxyla-ted-- (i.e., insert a "y" after the "x").

Signed and Sealed this

Twenty-eighth Day of September, 1993

Attest:

BRUCE LEHMAN

Attesting Officer

Commissioner of Patents and Trademarks